United States Patent
Ebanks et al.

(10) Patent No.: US 11,058,626 B2
(45) Date of Patent: *Jul. 13, 2021

(54) LONG-WEAR COMPOSITIONS CONTAINING SILICONE ACRYLATE COPOLYMER, SILICONE ELASTOMER RESIN AND SURFACE-TREATED PIGMENT

(71) Applicant: L'ORÉAL, Paris (FR)

(72) Inventors: Jody Ebanks, Bloomfield, NJ (US); Mariko Hasebe, New York, NY (US); Hy Si Bui, Piscataway, NJ (US)

(73) Assignee: L'OREAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/421,355

(22) Filed: Jan. 31, 2017

(65) Prior Publication Data

US 2018/0214367 A1  Aug. 2, 2018

(51) Int. Cl.
*A61K 8/893* (2006.01)
*A61K 8/895* (2006.01)
*A61Q 1/10* (2006.01)
*A61K 8/02* (2006.01)

(52) U.S. Cl.
CPC ............ *A61K 8/893* (2013.01); *A61K 8/0241* (2013.01); *A61K 8/895* (2013.01); *A61Q 1/10* (2013.01); *A61K 2800/43* (2013.01); *A61K 2800/544* (2013.01); *A61K 2800/61* (2013.01)

(58) Field of Classification Search
CPC ........ A61K 8/893; A61K 8/895; A61K 8/024; A61Q 1/10
See application file for complete search history.

(56) References Cited

U.S. PATENT DOCUMENTS

| | | | |
|---|---|---|---|
| 8,658,141 B2 | 2/2014 | Bui et al. | |
| 8,715,626 B2 | 5/2014 | Tamura et al. | |
| 8,784,787 B2 | 7/2014 | Tamura et al. | |
| 8,945,525 B2 | 2/2015 | Bradshaw et al. | |
| 9,133,309 B2 | 9/2015 | Iimura et al. | |
| 9,221,952 B2 | 12/2015 | Hayashi et al. | |
| 9,260,607 B2 | 2/2016 | Iimura et al. | |
| 2007/0093619 A1 | 4/2007 | Bui et al. | |
| 2010/0310489 A1* | 12/2010 | Barba | A61K 8/891 424/70.121 |
| 2012/0207801 A1* | 8/2012 | Sandstrom | A61Q 1/06 424/401 |
| 2012/0237583 A1 | 9/2012 | Hayashi et al. | |
| 2012/0251605 A1 | 10/2012 | Iimura et al. | |
| 2012/0269748 A1 | 10/2012 | Tamura et al. | |
| 2012/0269754 A1* | 10/2012 | Sandstrom | A61K 8/31 424/64 |
| 2012/0269875 A1 | 10/2012 | Tamura et al. | |
| 2012/0328539 A1 | 12/2012 | Tamura et al. | |
| 2013/0177516 A1 | 7/2013 | Tamura et al. | |
| 2014/0187649 A1 | 7/2014 | Tamura et al. | |
| 2014/0364394 A1 | 12/2014 | Tamura et al. | |
| 2014/0371330 A1 | 12/2014 | Hayashi et al. | |
| 2016/0008260 A1 | 1/2016 | Creutz et al. | |

FOREIGN PATENT DOCUMENTS

| | | |
|---|---|---|
| EP | 1 944 015 | 7/2008 |
| EP | 2 000 128 | 12/2008 |
| EP | 2 181 700 A1 | 5/2010 |
| EP | 2 492 333 B1 | 4/2014 |
| JP | 2006-058385 | 3/2006 |
| JP | 2010-143833 A | 7/2010 |
| JP | 2011-016734 | 1/2011 |
| JP | 2011-126807 | 6/2011 |
| JP | 2011-126808 | 6/2011 |
| JP | 2012-140343 A | 7/2012 |
| JP | 2013-001672 A | 1/2013 |
| JP | 2014-227358 A | 12/2014 |
| JP | 2015-137252 A | 7/2015 |
| JP | 5825871 B2 | 12/2015 |
| JP | 2016-008200 A | 1/2016 |
| KR | 2009/0054540 * | 6/2009 |
| WO | WO 2011/136389 A2 | 11/2011 |
| WO | WO 2012/2095399 | 7/2012 |
| WO | WO 2013/065766 A1 | 5/2013 |
| WO | WO 2013/065767 A1 | 5/2013 |

OTHER PUBLICATIONS

Jin et al., KR 2009/0054540, published: Jun. 1, 2009, English machine translation obtained on May 23, 2018.*
Tallarida (Quantitative Methods for Assessing Drug Synergism, Genes Cancer, Nov. 2011, 2(11), 1003-1008).*

* cited by examiner

*Primary Examiner* — Genevieve S Alley
(74) *Attorney, Agent, or Firm* — Oblon, McClelland, Maier & Neustadt, L.L.P.

(57) ABSTRACT

Compositions including at least one dendritic silicone acrylate copolymer, at least one silicone elastomer resin, and at least one surface-treated pigment, as well as methods of making such compositions and methods of applying such compositions to keratinous material are provided.

21 Claims, No Drawings

LONG-WEAR COMPOSITIONS CONTAINING SILICONE ACRYLATE COPOLYMER, SILICONE ELASTOMER RESIN AND SURFACE-TREATED PIGMENT

FIELD OF THE INVENTION

The present invention relates to compositions comprising at least one dendritic silicone acrylate copolymer, at least one silicone elastomer resin, and at least one surface-treated pigment. Among other improved or beneficial properties, these compositions have surprisingly good long-wear and/or transfer-resistance properties.

DISCUSSION OF THE BACKGROUND

Many cosmetic compositions, including pigmented cosmetics such as foundations, mascaras and lipsticks, have been formulated in an attempt to possess long wearing properties upon application. Unfortunately, many of these compositions do not generally possess both good long-wear/transfer-resistance properties as well as good application properties, good comfort properties and/or good appearance properties (for example, matte properties).

For example, with respect to lip compositions, commercial products containing silicon resins such as MQ resins are known. Such products are known to provide good long wear properties and/or transfer-resistance. However, such products possess poor application properties and/or poor feel upon application (for example, feels rough). Therefore, a second composition (topcoat) is separately applied to such products to improve poor properties of the compositions to make the products acceptable to consumers. Furthermore, the topcoat composition must be reapplied continually so that the product remains acceptable to consumers, meaning that the products are effectively not "long-wearing" as they require constant maintenance and reapplication.

Also, with respect to foundations, such products can provide good long wear properties and/or transfer-resistance. However, such long-wearing/transfer-resistant products can possess poor application and/or feel upon properties application, as well as poor matte properties.

Thus, there remains a need for improved compositions having improved cosmetic properties, particularly good wear, transfer-resistance, smudge-resistance, feel and/or matte characteristics upon application.

Accordingly, one aspect of the present invention is a care and/or makeup and/or treatment composition for keratinous materials which has good cosmetic properties such as, for example, good wear, transfer-resistance, smudge-resistance, feel and/or matte properties upon application, and which can be applied without having to engage in a multi-step application process.

SUMMARY OF THE INVENTION

The present invention relates to compositions comprising at least one dendritic silicone acrylate copolymer, at least one silicone elastomer resin, and at least one surface-treated pigment.

The present invention also relates to emulsion compositions comprising water, at least one dendritic silicone acrylate copolymer, at least one silicone elastomer resin, and at least one surface-treated pigment.

The present invention also relates to anhydrous compositions comprising at least one dendritic silicone acrylate copolymer, at least one silicone elastomer resin, and at least one surface-treated pigment.

The present invention also relates to colored compositions comprising at least one dendritic silicone acrylate copolymer, at least one silicone elastomer resin, and at least one surface-treated pigment.

The present invention also relates to methods of treating, caring for and/or making up keratinous materials such as, for example, lips, skin or eyelashes, by applying compositions of the present invention to a keratinous material in an amount sufficient to treat, care for and/or make up the keratinous material.

The present invention also relates to methods of enhancing the appearance of keratinous materials such as, for example, lips, skin or eyelashes, by applying compositions of the present invention to a keratinous material in an amount sufficient to enhance the appearance of the keratinous material.

It is to be understood that both the foregoing general description and the following detailed description are exemplary and explanatory only, and are not restrictive of the invention.

DETAILED DESCRIPTION OF THE INVENTION

As used herein, the expression "at least one" means one or more and thus includes individual components as well as mixtures/combinations.

Other than in the operating examples, or where otherwise indicated, all numbers expressing quantities of ingredients and/or reaction conditions are to be understood as being modified in all instances by the term "about," meaning within 10% to 15% of the indicated number.

"Film former" or "film forming agent" as used herein means any material such as, for example, a polymer or a resin that leaves a film on the substrate to which it is applied.

"Polymer" as used herein means a compound which is made up of at least two monomers.

"Keratinous materials" includes materials containing keratin such as hair, skin, eyebrows, lips and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen containing groups, ester groups, thiol groups, sulphonate groups, thiosulphate groups, siloxane groups, hydroxyalkyl groups, and polysiloxane groups. The substituent(s) may be further substituted.

"Volatile", as used herein, means having a flash point of less than about 100° C.

"Non-volatile", as used herein, means having a flash point of greater than about 100° C.

"Anhydrous" means the compositions contain less than 1% water. Preferably, the compositions of the present invention contain less than 0.5% water, and most preferably no water.

"Transfer" as used herein refers to the displacement of a fraction of a composition which has been applied to a keratinous material by contact with another substrate, whether of the same nature or of a different nature. For example, when a composition such as an eyeshadow, eyeliner or mascara has been applied, the composition can be transferred onto hands by rubbing or by contact of the hands with the eyes. By way of further example, when a composition such as a lipstick has been applied, the composition can be transferred onto teeth or hands, or onto the cheek of another person. Irrespective of composition type, the composition can also transfer from the keratinous material to which it has been applied to another substrate such as napkins, collars, glasses, cups or other containers.

"Transfer-resistance" as used herein refers to the quality exhibited by a composition in resisting transfer. To determine transfer-resistance, the amount of composition transferred from a keratinous material to a substrate may be evaluated and compared. For example, a composition may be transfer-resistant if, after application to a keratinous material such as lips, skin or eyelashes and contact with a substrate, a majority of the composition is left on the wearer. Further, the amount transferred may be compared with that transferred by other compositions, such as commercially-available compositions. In a preferred embodiment of the present invention, little or no composition is transferred to the substrate from the keratinous material.

"Long wear" compositions as used herein refers to compositions where the compositions, after application to a keratinous material, do not transfer or smudge after contact with another substrate and retain a consistent appearance on the keratinous material for an extended period of time. "Long wear" compositions, as used herein can also refer to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to keratinous materials such as skin, eyelashes or lips and evaluating the color of the composition after an extended period of time. For example, the color of a composition may be evaluated immediately following application to the keratinous material and these characteristics may then be re-evaluated and compared after a certain amount of time. Further, these characteristics may be evaluated with respect to other compositions, such as commercially available compositions. Additionally, long wear properties may be evaluated by applying a sample, allowing it to dry, and then abrading the sample to determine removal/loss of sample.

The composition of the present invention may be in any form, either liquid or non-liquid (semi-solid, soft solid, solid, etc.). For example, it may be a paste, a solid, a gel, or a cream. It may be an emulsion, such as an oil-in-water or water-in-oil emulsion, a multiple emulsion, such as an oil-in-water-in-oil emulsion or a water-in-oil-in-water emulsion, or a solid, rigid or supple gel. The composition of the invention may, for example, comprise an external or continuous fatty phase. The composition can also be a molded composition or cast as a stick or a dish.

The compositions and methods of the present invention can comprise, consist of, or consist essentially of the essential elements and limitations of the invention described herein, as well as any additional or optional ingredients, components, or limitations described herein or otherwise useful in personal care.

In accordance with the present invention, compositions comprising at least one dendritic silicone acrylate copolymer, at least one silicone elastomer resin, and at least one surface-treated pigment are provided.

Surface-Treated Pigment

In accordance with the present invention, compositions comprising at least one surface-treated pigment are provided. "Surface-treated pigment" means pigments that have totally or partially undergone a surface treatment of chemical, electronic, electrochemical, mechanochemical or mechanical nature, with a surface treatment agent. Preferably, the pigments are selected from inorganic pigments or inorganic/organic mixed pigments.

In accordance with the present invention, surface treatment agents are selected from the group consisting of metal salts of fatty acids, organosilanes, halogenated phosphonates and halogenated organosilanes. According to preferred embodiments, pigments have been surface treated with a surface treatment agent selected from the group consisting of metal salts of fatty acids such as, for example, magnesium, iron, titanium, zinc or aluminum salts of fatty acids, including organotitanate compounds; organosilanes; halogenated organophosphonates such as, for example, perfluoroalkyl phosphonates, and salts thereof; and halogenated organosilanes such as, for example, perfluoroalkyl silanes, and salts thereof. Specific examples of suitable surface treatment agents include (1) perfluorooctyltriethoxysilane, (2) perfluorooctyltriethoxysilane/acrylates dimethicone copolymer, (3) perfluorooctyltriethoxysilane/triethoxy caprylylsilane, (4) sodium perfluorohexylethylphosphonate and (5) iron oxide (and) isopropyl titanium triisosterate (and) triethoxysilylethyl polydimethylsiloxy ethyl dimethicone.

The surface-treated pigments of the present invention can be prepared according to surface treatment techniques well known to a person of ordinary skill in the art or can be found commercially.

For example, the surface treatment agent with which the pigments are treated can be deposited on the pigments by solvent evaporation, chemical reaction between the molecules of the surface treatment agent or creation of a covalent bond between the surface treatment agent and the pigments. The surface treatment can thus be carried out, for example, by chemical reaction of a surface treatment agent with the surface of the pigments and creation of a covalent bond between the surface treatment agent and the pigments. An exemplary method is described, for example, in U.S. Pat. No. 4,578,266, the entire contents of which is hereby incorporated by reference.

The surface-treated pigment preferably is present in the compositions of the present invention in an active solid content amount ranging from about 1% to about 30%, preferably from about 3% to about 25%, and preferably from about 5% to about 20%, by weight with respect to the total weight of the composition, including all ranges and subranges therebetween.

Dendritic Silicone Acrylate Copolymers

In accordance with the present invention, compositions comprising at least one dendritic silicone acrylate copolymer are provided. Suitable dendritic silicone acrylate copolymers include branched polymers comprising at least one siloxane group and at least one hydrocarbon group.

Suitable hydrocarbon groups in such copolymers include, for example, vinyl groups, methacrylate groups and/or acrylate groups.

Suitable siloxane groups include, for example, those referred to in the art as M, D, T and Q units. The letter M represents the monofunctional unit, for example, of formula $(CH_3)_3SiO_{1/2}$, the silicon atom being connected to only one oxygen atom in the polymer comprising this unit. The letter D means a difunctional unit, for example, $(CH_3)_2SiO_{2/2}$ in which the silicon atom is connected to two oxygen atoms. The letter T represents a trifunctional unit, for example, of formula $(CH_3)SiO_{3/2}$. The letter Q means a tetrafunctional unit $SiO_{4/2}$ in which the silicon atom is bonded to four hydrogen atoms, which are themselves bonded to the rest of the polymer.

Specific examples of suitable dendritic silicone acrylate copolymers include the acrylate/dimethicone copolymers sold by Dow Corning under the tradenames FA 4001 CM SILICONE ACRYLATE (cyclopentasiloxane (and) acrylates/polytrimethylsiloxymethacrylate copolymer), FA 4002 ID SILICONE ACRYLATE (isododecane (and) acrylates/polytrimethylsiloxymethacrylate copolymer), FA 4003 DM SILICONE ACRYLATE (dimethicone (and) acrylates/polytrimethylsiloxymethacrylate copolymer), and FA 4004 ID SILICONE ACRYLATE (isododecane (and) acrylates/polytrimethylsiloxymethacrylate copolymer), and mixtures thereof.

Suitable examples of dendritic silicone acrylate copolymers can be found in U.S. Pat. No. 8,784,787, the entire contents of which is hereby incorporated by reference. As described in the '787 patent, suitable copolymers can have a group that has a siloxane dendron structure ($L^1$) and a hydrophilic group (Q) as expressed in the following general formula (1):

$$R^1{}_a L^1{}_b Q_c SiO_{(4-a-b-c)/2} \quad (1)$$

where:

$R^1$ is a monovalent organic group or a hydrogen atom. However, $R^1$ as a monovalent organic group does not include groups that correspond to $L^1$ or Q. Examples of the $R^1$ moiety include a hydrogen atom, a substituted or unsubstituted monovalent hydrocarbon group having from 1 to 30 carbons, an alkoxy group having from 1 to 30 carbons, a straight or branched polysiloxane chain, and the like. Examples of the substituted or unsubstituted monovalent hydrocarbon group include methyl groups, ethyl groups, propyl groups, butyl groups, pentyl groups, hexyl groups, heptyl groups, octyl groups, decyl groups, dodecyl groups, and other similar saturated aliphatic hydrocarbon groups; cyclopentyl groups, cyclohexyl groups, and similar saturated cycloaliphatic hydrocarbon groups; phenyl groups, tolyl groups, xylyl groups, naphthyl groups, and similar aromatic hydrocarbon groups; and groups wherein the hydrogen atoms bonded to the carbon atoms of these groups are substituted at least partially by fluorine or a similar halogen atom, or an organic group having an epoxy group, an acyl group, a carboxyl group, an amino group, a (meth) acryl group, a mercapto group, or the like. Examples of the alkoxy group include methoxy groups, ethoxy groups, isopropanoxy groups, higher alkoxy groups, and the like. The straight or branched polysiloxane chain is a straight or branched polysiloxane chain that does not correspond with $L^1$. Examples thereof include straight or branched polysiloxane chains having a polysiloxane chain structure that comprises a dimethylpolysiloxane unit that is bonded to the siloxane via a divalent linking group; where the dimethylpolysiloxane unit has a degree of polymerization of 1 to 100, and a silanol end, a trimethylsiloxy end, or an n-butyldimethylsiloxy end. Note that a portion of the methyl group of the polysiloxane chain may be substituted by a phenyl group, a fluorine or similar halogen atom, or an organic group including epoxy groups, acyl groups, carboxyl groups, amino groups, (meth)acryl groups, mercapto groups, and the like.

A modified group other than the group having a siloxane dendron structure (-$L^1$) and the hydrophilic group (-Q) can be introduced as $R^1$. Specifically, when $R^1$ is a substituted monovalent hydrocarbon group, a substituent can be suitably selected from the organic group examples described above in accordance with desired characteristics and uses. For example, a monovalent hydrocarbon group substituted with an amino group, an aminoethyl aminopropyl group, a carboxyl group, or the like can be selected. Likewise, in addition to an alkyl group having from 1 to 4 carbons such as a methyl group or an ethyl group, an alkyl group having from 8 to 20 carbons can be selected as a portion of the $R^1$ moiety. Of these, $R^1$ is preferably a monovalent hydrocarbon group or a monovalent fluorinated hydrocarbon group having from 1 to 20 carbons. Examples of the monovalent hydrocarbon group not having unsaturated aliphatic bonds belonging to the $R^1$ moiety include methyl groups, ethyl groups, propyl groups, butyl groups, pentyl groups, hexyl groups, and similar alkyl groups; phenyl groups, tolyl groups, xylyl groups, and similar aryl groups; and aralkyl groups such as benzyl groups. Examples of the monovalent fluorinated hydrocarbon group include trifluoropropyl groups, pentafluoroethyl groups, and similar perfluoroalkyl groups. Preferably, $R^1$ is a methyl group, an ethyl group, and/or a phenyl group, and preferably from 90 to 100 mol % of all the $R^1$ moieties are selected from the group consisting of methyl groups, ethyl groups, and phenyl groups.

$L^1$ is a silylalkyl group having a siloxane dendron structure, and is defined as the silylalkyl group expressed by the following general formula (2) when i=1.

General Formula (2)

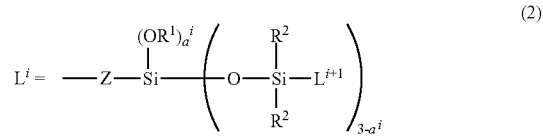

The silylalkyl group having a siloxane dendron structure has a structure where a carbosiloxane unit is extended in the form of a dendrimer. $R^2$ is a phenyl group or an alkyl group having from 1 to 6 carbons. Examples of the alkyl group having from 1 to 6 carbons include methyl, ethyl, n-propyl, i-propyl, n-butyl, i-butyl, s-butyl, pentyl, neopentyl, cyclopentyl, hexyl, and similar straight, branched, or cyclic alkyl groups. $R^1$ is a group that is synonymous with that described above and, in the general formula (2), is preferably a hydrogen atom, or a substituted or unsubstituted monovalent hydrocarbon group having from 1 to 30 carbons, and more preferably is a methyl group or a hydrogen atom.

In general formula (2), i represents a generation of the silylalkyl group represented by $L^i$, and is an integer of 1 to c when c is a number of generations that is a number of repetitions of the silylalkyl group. The number of generations c is an integer from 1 to 10, and $L^{i+1}$ is the silylalkyl group when i is less than c and is a methyl group or a phenyl group when i=c. $L^{i+1}$ is preferably a methyl group when i=c. $a^i$ is a number in a range of 0 to 3. The number of generations c is preferably an integer from 1 to 3, and more preferably is 1 or 2.

The dendritic silicone acrylate copolymer is preferably present in the compositions of the present invention in an active solid content amount ranging from about 0.1% to about 30%, preferably from about 0.75% to about 25%, and preferably from about 1% to about 20%, by weight with respect to the total weight of the composition, including all ranges and subranges there between.

According to preferred embodiments, the dendritic silicone acrylate copolymer and surface-treated pigment are present in the compositions of the present invention in an active solid content weight ratio of 1:300 to 30:1, preferably a weight ratio of 1:34 to 25:3, and preferably a weight ratio of 1:20 to 4:1, including all ranges and subranges therebetween.

Silicone Elastomer Resin

In accordance with the present invention, compositions comprising at least one silicone elastomer resin are provided. A "silicone elastomer resin" is a compound which comprises a "silicone elastomer" portion and a "resin" portion. Silicone elastomer resins are described or referenced in U.S. Pat. Nos. 8,987,373 and 9,175,139 as well as in U.S. patent application publication no. 2015/0073059, the entire contents of all of which are hereby incorporated by reference.

The silicone elastomer resin preferably has a particle size ranging from 0.1 to 500 µm, preferably from 3 to 200 µm and preferably from 3 to 50 µm. The silicone elastomer resin can have any shape and, for example, can be spherical, flat or amorphous.

According to preferred embodiments, when placed in solvent, the silicone elastomer resin does not substantially swell (as opposed to typical silicone elastomers which swell upon introduction into solvent). Preferably, when placed in solvent, the silicone elastomer resin swells (increases in size) by less than 10% of the size of the silicone elastomer resin (in an unswelled state), preferably less than 7.5% of the size of silicone elastomer resin (in an unswelled state), preferably less than 5% of the size of silicone elastomer resin (in an unswelled state), preferably less than 2.5% of the size of silicone elastomer resin (in an unswelled state), preferably less than 1% of the size of silicone elastomer resin (in an unswelled state).

With respect to the silicone elastomer portion, this portion corresponds to polyorganosiloxanes commonly known as silicone elastomers. "Elastomer" is generally understood in the art to mean a flexible and deformable solid material having viscoelastic properties. However, its modulus of elasticity is such that it is resistant to deformation and has a limited ability to expand and to contract.

The silicone elastomer portion is preferably partially or completely crosslinked. The degree of crosslinking can vary depending on the elastic properties desired. Cross-linking materials may be hydrophilic (ethylene oxide and propylene oxide, for example), hydrophobic (dimethicone, vinyl dimethicone, alkyl, etc.) or combinations thereof.

The silicone elastomer portion preferably has a particle size ranging from 0.1 to 500 µm, preferably from 3 to 200 µm and preferably from 3 to 50 µm. The portion can have any shape and, for example, can be spherical, flat or amorphous.

Crosslinking can be obtained, for example, by a crosslinking addition reaction of a diorganopolysiloxane comprising at least one hydrogen atom bonded to a silicon atom and a diorganopolysiloxane having at least two groups comprising ethylenic unsaturation bonded to separate silicon atoms, in particular in the presence of a platinum catalyst; or by a crosslinking condensation/dehydrogenation reaction between a diorganopolysiloxane comprising hydroxyl endings and a diorganopolysiloxane comprising at least one hydrogen atom bonded to a silicon atom, in particular in the presence of an organotin compound; or by a crosslinking condensation reaction of a diorganopolysiloxane comprising hydroxyl endings and of a hydrolysable organopolysilane; or by thermal crosslinking of an organopolysiloxane, in particular in the presence of an organoperoxide catalyst; or by crosslinking of an organopolysiloxane by high energy radiation, such as gamma rays, ultraviolet rays or an electron beam.

Crosslinking can be obtained, for example, by a crosslinking addition reaction (A) of a diorganopolysiloxane comprising at least one hydrogen atom bonded to a silicon atom and (B) of a diorganopolysiloxane having at least two groups comprising ethylenic unsaturation each bonded to a separate silicon atom, in particular in the presence (C) of a platinum catalyst, as, for example, disclosed in Application EP-A-295 886.

The organic groups bonded to the silicon atoms of the compound (A) can be alkyl groups, such as methyl, ethyl, propyl, butyl or octyl; substituted alkyl groups, such as 2-phenylethyl, 2-phenylpropyl or 3,3,3-trifluoropropyl; aryl groups, such as phenyl, tolyl or xylyl; substituted aryl groups, such as phenylethyl; and substituted monovalent hydrocarbonaceous groups, such as an epoxy group, a carboxylate ester group or a mercapto group. The compound (A) can thus be chosen from methylhydropolysiloxanes comprising trimethylsiloxy endings, dimethylsiloxane/methylhydrosiloxane copolymers comprising trimethylsiloxy endings or dimethylsiloxane/methylhydrosiloxane cyclic copolymers.

The compound (B) is advantageously a diorganopolysiloxane having at least two lower (for example $C_{2-4}$) alkenyl groups; the lower alkenyl group can be chosen from vinyl, allyl and propenyl groups. These lower alkenyl groups can be situated in any position on the organopolysiloxane molecule but are preferably situated at the ends of the organopolysiloxane molecule. The organopolysiloxane (B) can have a branched-chain, linear-chain, cyclic or network structure but the linear-chain structure is preferred. In addition to the abovementioned alkenyl groups, the other organic groups bonded to the silicon atoms in the compound (B) can be alkyl groups, such as methyl, ethyl, propyl, butyl or octyl; substituted alkyl groups, such as 2-phenylethyl, 2-phenylpropyl or 3,3,3-trifluoropropyl; aryl groups, such as phenyl, tolyl or xylyl; substituted aryl groups, such as phenylethyl; and substituted monovalent hydrocarbonaceous groups, such as an epoxy group, a carboxylate ester group or a mercapto group. The organopolysiloxanes (B) can be chosen from methylvinylpolysiloxanes, methylvinylsiloxane/dimethylsiloxane copolymers, dimethylpolysiloxanes comprising dimethylvinylsiloxy endings, dimethylsiloxane/methylphenylsiloxane copolymers comprising dimethylvinylsiloxy endings, dimethylsiloxane/diphenylsiloxane/methylvinylsiloxane copolymers comprising dimethylvinylsiloxy endings, dimethylsiloxane/methylvinylsiloxane copolymers comprising trimethylsiloxy endings, dimethylsiloxane/methylphenylsiloxane/methylvinylsiloxane copolymers comprising trimethylsiloxy endings, methyl(3,3,3-trifluoropropyl)polysiloxanes comprising dimethylvinylsiloxy endings and dimethylsiloxane/methyl(3,3,3-trifluoropropyl)siloxane copolymers comprising dimethylvinylsiloxy endings.

According to preferred embodiments, crosslinking is at least partially accomplished by the resin portion. Preferably, the crosslinking in the silicone elastomer resin is due only to the resin portion.

With respect to the resin portion, using the same silicone resin nomenclature ("MDTQ") as discussed above, the resin portion can be described according to the various monomeric siloxane units which make up the polymer.

The letter M represents the monofunctional unit, for example, of formula $(CH_3)_3SiO_{1/2}$, the silicon atom being connected to only one oxygen atom in the polymer comprising this unit.

The letter D means a difunctional unit, for example, $(CH_3)_2SiO_{2/2}$ in which the silicon atom is connected to two oxygen atoms.

The letter T represents a trifunctional unit, for example, of formula $(CH_3)SiO_{3/2}$.

The letter Q means a tetrafunctional unit $SiO_{4/2}$ in which the silicon atom is bonded to four hydrogen atoms, which are themselves bonded to the rest of the polymer.

So, for example, the resin portion can be a T resin, a MQ resin ("trimethylsiloxysilicate"), a MT resin, a MDT resin, a MDQ resin, etc.

In the M, D and T units listed as examples above, at least one of the methyl groups may be substituted with a hydrocarbon-based group containing from 1 to 10 carbon atoms or a hydroxyl group. According to preferred embodiments, the hydrocarbon-based group containing from 1 to 10 carbon atoms is a methyl group.

Suitable examples of silicone elastomer resins include vinyldimethyl/trimethylsiloxysilicate stearyl dimethicone crosspolymer, available as BELSIL® RG 90 elastomer gel (Isododecane (and) Vinyldimethyl/trimethylsiloxysilicate stearyl dimethicone crosspolymer) from Wacker; Dimethicone/Vinyltrimethylsiloxysilicate Crosspolymer, available as BELSIL® REG 1102 (DIMETHICONE, DIMETHICONE/VINYLTRIMETHYLSILOXYSILICATE CROSSPOLYMER) from Wacker; and Dimethicone/Vinyltrimethylsiloxysilicate Crosspolymer, available as BELSIL® REG 102 (Cyclopentasiloxane, Dimethicone/Vinyltrimethylsiloxysilicate Crosspolymer) from Wacker.

The silicone elastomer resins can be dissolved in a suitable solvent, either prior to their introduction into the composition of the invention, or in situ within the composition. Examples of suitable solvents, include, but are not limited to, volatile and non-volatile silicones, volatile and non-volatile alcohols, volatile and non-volatile esters, volatile and non-volatile hydrocarbons and mixtures thereof.

The silicone elastomer resin preferably is present in the compositions of the present invention in an active solid content amount ranging from about 0.1% to about 15%, preferably from about 0.5% to about 12%, and preferably from about 1% to about 10%, by weight with respect to the total weight of the composition, including all ranges and subranges therebetween.

According to preferred embodiments, the dendritic silicone acrylate copolymer and silicone elastomer resin are present in the compositions of the present invention in an active solid content weight ratio of 1:300 to 400:1, preferably a weight ratio of 1:50 to 70:1, and preferably a weight ratio of 1:20 to 30:1, including all ranges and subranges therebetween.

According to preferred embodiments, the surface-treated pigment and silicone elastomer resin are present in the compositions of the present invention in an active solid content weight ratio of 1:15 to 300:1, preferably a weight ratio of 1:4 to 50:1, and preferably a weight ratio of 1:2 to 20:1, including all ranges and subranges therebetween.

Coloring Agents

According to preferred embodiments of the present invention, compositions further comprising at least one coloring agent are provided. Such coloring agents, if present, are in addition to the surface-treated pigment discussed above.

According to this embodiment the coloring agent is preferably chosen from pigments which are not surface-treated, dyes, such as liposoluble dyes, nacreous pigments, and pearling agents.

Representative liposoluble dyes which may be used according to the present invention include Sudan Red, DC Red 17, DC Green 6, ß-carotene, soybean oil, Sudan Brown, DC Yellow 11, DC Violet 2, DC Orange 5, annatto, and quinoline yellow. The liposoluble dyes, when present, generally have a concentration ranging up to 40% by weight of the total weight of the composition, such as from 0.0001% to 30%, including all ranges and subranges therebetween.

The nacreous pigments which may be used according to the present invention may be chosen from colored nacreous pigments such as titanium mica with iron oxides, titanium mica with ferric blue or chromium oxide, titanium mica with an organic pigment chosen from those mentioned above, and nacreous pigments based on bismuth oxychloride. The nacreous pigments, if present, be present in the composition in a concentration ranging up to 50% by weight of the total weight of the composition, such as from 0.0001% to 40%, preferably from 0.001% to 30%, including all ranges and subranges therebetween.

The non-surface treated pigments, which may be used according to the present invention, may be chosen from white, colored, inorganic, organic, polymeric, and nonpolymeric pigments. Representative examples of mineral pigments include titanium dioxide, zirconium oxide, zinc oxide, cerium oxide, iron oxides, chromium oxides, manganese violet, ultramarine blue, chromium hydrate, and ferric blue. Representative examples of organic pigments include carbon black, pigments of D & C type, and lakes based on cochineal carmine, barium, strontium, calcium, and aluminum.

If present, the coloring agents may be present in the composition in a concentration ranging up to 50% by weight of the total weight of the composition, such as from 0.0001% to 40%, and further such as from 0.001% to 30%, including all ranges and subranges therebetween.

Oil Phase

According to preferred embodiments of the present invention, compositions further comprising at least one fatty substance are provided. Suitable fatty substances include oil(s) and/or wax(es). "Oil" means any non-aqueous medium which is liquid at ambient temperature (25° C.) and atmospheric pressure (760 mm Hg). A "wax" for the purposes of the present disclosure is a lipophilic fatty compound that is solid at ambient temperature (25° C.) and changes from the solid to the liquid state reversibly, having a melting temperature of more than 30° C. and, for example, more than 45° C., which can be as high as 150° C., a hardness of more than 0.5 MPa at ambient temperature, and an anisotropic crystalline organization in the solid state. By taking the wax to its melting temperature, it is possible to use wax(es) by themselves as carriers and/or it is possible to make wax(es) miscible with the oils to form a microscopically homogeneous mixture.

Suitable oils include volatile and/or non-volatile oils. Such oils can be any acceptable oil including but not limited to silicone oils and/or hydrocarbon oils.

According to certain embodiments, the compositions of the present invention preferably comprise one or more volatile silicone oils. Examples of such volatile silicone oils include linear or cyclic silicone oils having a viscosity at room temperature less than or equal to 6 cSt and having from 2 to 7 silicon atoms, these silicones being optionally substituted with alkyl or alkoxy groups of 1 to 10 carbon atoms.

Specific oils that may be used in the invention include octamethyltetrasiloxane, decamethylcyclopentasiloxane, dodecamethylcyclohexasiloxane, heptamethyloctyltrisiloxane, hexamethyldisiloxane, decamethyltetrasiloxane, dodecamethylpentasiloxane and their mixtures. Other volatile oils which may be used include KF 96A of 6 cSt viscosity, a commercial product from Shin Etsu having a flash point of 94° C. Preferably, the volatile silicone oils have a flash point of at least 40° C.

Non-limiting examples of volatile silicone oils are listed in Table 1 below.

TABLE 1

| Compound | Flash Point (° C.) | Viscosity (cSt) |
| --- | --- | --- |
| Octyltrimethicone | 93 | 1.2 |
| Hexyltrimethicone | 79 | 1.2 |
| Decamethylcyclopentasiloxane (cyclopentasiloxane or D5) | 72 | 4.2 |
| Octamethylcyclotetrasiloxane (cyclotetradimethylsiloxane or D4) | 55 | 2.5 |
| Dodecamethylcyclohexasiloxane (D6) | 93 | 7 |
| Decamethyltetrasiloxane(L4) | 63 | 1.7 |
| KF-96 A from Shin Etsu | 94 | 6 |
| PDMS (polydimethylsiloxane) DC 200 (1.5 cSt) from Dow Corning | 56 | 1.5 |
| PDMS DC 200 (2 cSt) from Dow Corning | 87 | 2 |

Further, a volatile linear silicone oil may be employed in the present invention. Suitable volatile linear silicone oils include those described in U.S. Pat. No. 6,338,839 and WO03/042221, the contents of which are incorporated herein by reference. In one embodiment the volatile linear silicone oil is decamethyltetrasiloxane. In another embodiment, the decamethyltetrasiloxane is further combined with another solvent that is more volatile than decamethyltetrasiloxane.

According to certain embodiments of the present invention, the composition of preferably comprises one or more non-silicone volatile oils and may be selected from volatile hydrocarbon oils, volatile esters and volatile ethers. Examples of such volatile non-silicone oils include, but are not limited to, volatile hydrocarbon oils having from 8 to 16 carbon atoms and their mixtures and in particular branched $C_8$ to $C_{16}$ alkanes such as $C_8$ to $C_{16}$ isoalkanes (also known as isoparaffins), isohexacecane, isododecane, isodecane, and for example, the oils sold under the trade names of Isopar or Permethyl. Preferably, the volatile non-silicone oils have a flash point of at least 40° C.

Non-limiting examples of volatile non-silicone volatile oils are given in Table 2 below.

TABLE 2

| Compound | Flash Point (° C.) |
| --- | --- |
| Isododecane | 43 |
| Propylene glycol n-butyl ether | 60 |
| Ethyl 3-ethoxypropionate | 58 |
| Propylene glycol methylether acetate | 46 |
| Isopar L (isoparaffin $C_{11}$-$C_{13}$) | 62 |
| Isopar H (isoparaffin $C_{11}$-$C_{12}$) | 56 |

The volatility of the solvents/oils can be determined using the evaporation speed as set forth in U.S. Pat. No. 6,338,839, the contents of which are incorporated by reference herein.

According to certain embodiments of the present invention, the composition comprises at least one non-volatile oil.

Examples of non-volatile oils that may be used in the present invention include, but are not limited to, polar oils such as:

hydrocarbon-based plant oils with a high triglyceride content consisting of fatty acid esters of glycerol, the fatty acids of which may have varied chain lengths, these chains possibly being linear or branched, and saturated or unsaturated; these oils are especially wheat germ oil, corn oil, sunflower oil, karite butter, castor oil, sweet almond oil, macadamia oil, apricot oil, soybean oil, rapeseed oil, cottonseed oil, alfalfa oil, poppy oil, pumpkin oil, sesame seed oil, marrow oil, avocado oil, hazelnut oil, grape seed oil, blackcurrant seed oil, evening primrose oil, millet oil, barley oil, *quinoa* oil, olive oil, rye oil, safflower oil, candlenut oil, passion flower oil or musk rose oil; or caprylic/capric acid triglycerides, for instance those sold by the company Stearineries Dubois or those sold under the names Miglyol 810, 812 and 818 by the company Dynamit Nobel;

synthetic oils or esters of formula $R_5COOR_6$ in which $R_5$ represents a linear or branched higher fatty acid residue containing from 1 to 40 carbon atoms, including from 7 to 19 carbon atoms, and $R_6$ represents a branched hydrocarbon-based chain containing from 1 to 40 carbon atoms, including from 3 to 20 carbon atoms, with $R_6+R_7 \geq 10$, such as, for example, Purcellin oil (cetostearyl octanoate), isononyl isononanoate, octyldodecyl neopentanoate, $C_{12}$ to $C_{15}$ alkyl benzoate, isopropyl myristate, 2-ethylhexyl palmitate, and octanoates, decanoates or ricinoleates of alcohols or of polyalcohols; hydroxylated esters, for instance isostearyl lactate or diisostearyl malate; and pentaerythritol esters;

synthetic ethers containing from 10 to 40 carbon atoms;

$C_8$ to $C_{26}$ fatty alcohols, for instance oleyl alcohol, cetyl alcohol, stearyl alcohol, and cetearly alcohol; and mixtures thereof.

Further, examples of non-volatile oils that may be used in the present invention include, but are not limited to, non-polar oils such as branched and unbranched hydrocarbons and hydrocarbon waxes including polyolefins, in particular Vaseline (petrolatum), paraffin oil, squalane, squalene, hydrogenated polyisobutene, hydrogenated polydecene, polybutene, mineral oil, pentahydrosqualene, and mixtures thereof.

According to preferred embodiments, if present, then at least one oil is present in the compositions of the present invention in an amount ranging from about 5 to about 80% by weight, more preferably from about 10 to about 70% by weight, and most preferably from about 15 to about 60% by weight, based on the total weight of the composition, including all ranges and subranges within these ranges.

According to preferred embodiments of the present invention, the compositions of the present invention further comprise at least one wax. Suitable examples of waxes that can be used in accordance with the present disclosure include those generally used in the cosmetics field: they include those of natural origin, such as beeswax, carnauba wax, candelilla wax, ouricoury wax, Japan wax, cork fibre wax or sugar cane wax, rice bran wax, rice wax, montan wax, paraffin wax, lignite wax or microcrystalline wax, ceresin or ozokerite, and hydrogenated oils such as hydrogenated castor oil or jojoba oil; synthetic waxes such as the polyethylene waxes obtained from the polymerization or copolymerization of ethylene, and Fischer-Tropsch waxes, or else esters of fatty acids, such as octacosanyl stearate, glycerides which are concrete at 30° C., for example at 45° C.

According to particularly preferred embodiments of the present invention, the compositions of the present invention further include at least one silicone wax. Examples of suitable silicone waxes include, but are not limited to, silicone waxes such as alkyl- or alkoxydimethicones having an alkyl or alkoxy chain ranging from 10 to 45 carbon atoms, poly(di)methylsiloxane esters which are solid at 30° C. and whose ester chain comprising at least 10 carbon atoms, di(1,1,1-trimethylolpropane) tetrastearate, which is sold or manufactured by Heterene under the name HEST 2T-4S; alkylated silicone acrylate copolymer waxes comprising at least 40 mole % of siloxy units having the formula $(R_2R'SiO_{1/2})_x(R''SiO_{3/2})_y$, where x and y have a value of 0.05 to 0.95, R is an alkyl group having from 1 to 8 carbon atoms, an aryl group, a carbinol group, or an amino group, R is a monovalent hydrocarbon having 9-40 carbon atoms, R" is a monovalent hydrocarbon group having 1 to 8 carbon atoms, an aryl group such as those disclosed in U.S. patent application Ser. No. 2007/0149703, the entire contents of which is hereby incorporated by reference, with a particular example being C30-C45 alkyldimethylsilyl polypropylsilsesquioxane; and mixtures thereof.

According to preferred embodiments of the present invention, the compositions of the present invention further include at least one long-chain alcohol wax. Preferably, the at least one long-chain alcohol wax has an average carbon chain length of between about 20 and about 60 carbon atoms, most preferably between about 30 and about 50 carbon atoms. Suitable examples of long-chain alcohol waxes include but are not limited to alcohol waxes commercially available from Baker Hughes under the Performacol trade name such as, for example, Performacol 350, 425 and 550. Most preferably, the long-chain alcohol wax has a melting temperature range from about 93° C. to about 105° C.

According to preferred embodiments, the compositions of the present invention contain less than 1% wax.

According to preferred embodiments, the compositions of the present invention contain less than 0.5% wax.

According to preferred embodiments, the compositions of the present invention contain no wax.

If present, the wax or waxes may be present in an amount ranging from 1 to 30% by weight relative to the total weight of the composition, for example from 2 to 20%, and for example from 3 to 10%, including all ranges and subranges therebetween.

Aqueous Phase

The compositions of the present invention may also contain water. When the compositions of the present invention contain water, they are preferably in the form of an emulsion. Preferably, when the compositions of the present invention contain water, they are in the form of an oil-in-water emulsion (O/W) or a water-in-oil emulsion (W/O). Preferably, when in the form of an emulsion, the oil phase contains predominantly silicone oils (Si/W or W/Si emulsion) or hydrocarbon oils. When present, water is preferably present in an amount of from about 10% to about 80% by weight, preferably from about 20% to about 70% by weight, preferably from about 35% to about 65% by weight, including all ranges and subranges therebetween, all weights being based on the total weight of the composition.

Additional Additives

The composition of the invention can also comprise any additive usually used in the field under consideration. For example, dispersants such as poly(12-hydroxystearic acid), antioxidants, essential oils, sunscreens, preserving agents, fragrances, fillers, neutralizing agents, cosmetic and dermatological active agents such as, for example, emollients, moisturizers, vitamins, essential fatty acids, surfactants, silicone elastomers, thickening agents, gelling agents, particles, pasty compounds, viscosity increasing agents can be added. A non-exhaustive listing of such ingredients can be found in U.S. patent application publication no. 2004/0170586, the entire contents of which is hereby incorporated by reference. Further examples of suitable additional components can be found in the other references which have been incorporated by reference in this application. Still further examples of such additional ingredients may be found in the *International Cosmetic Ingredient Dictionary and Handbook* ($9^{th}$ ed. 2002).

A person skilled in the art will take care to select the optional additional additives and/or the amount thereof such that the advantageous properties of the composition according to the invention are not, or are not substantially, adversely affected by the envisaged addition.

These substances may be selected variously by the person skilled in the art in order to prepare a composition which has the desired properties, for example, consistency or texture.

These additives may be present in the composition in a proportion from 0% to 99% (such as from 0.01% to 90%) relative to the total weight of the composition and further such as from 0.1% to 50% (if present), including all ranges and subranges therebetween.

Needless to say, the composition of the invention should be cosmetically or dermatologically acceptable, i.e., it should contain a non-toxic physiologically acceptable medium and should be able to be applied to the keratinous materials of human beings such as, for example, lips, skin or eyelashes.

In particular, suitable gelling agents for the oil phase include, but are not limited to, lipophilic or hydrophilic clays.

The term "hydrophilic clay" means a clay that is capable of swelling in water; this clay swells in water and forms after hydration a colloidal dispersion. These clays are products that are already well known per se, which are described, for example, in the book "Mineralogie des argiles", S. Caillere, S. Henin, M. Rautureau, $2^{nd}$ edition 1982, Masson, the teaching of which is included herein by way of reference. Clays are silicates containing a cation that may be chosen from calcium, magnesium, aluminium, sodium, potassium and lithium cations, and mixtures thereof. Examples of such products that may be mentioned include clays of the smectite family such as montmorillonites, hectorites, bentonites, beidellites and saponites, and also of the family of vermiculites, stevensite and chlorites. These clays may be of natural or synthetic origin.

Hydrophilic clays that may be mentioned include smectite products such as saponites, hectorites, montmorillonites, bentonites and beidellite. Hydrophilic clays that may be mentioned include synthetic hectorites (also known as laponites), for instance the products sold by the company Laporte under the names Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the products sold by the Vanderbilt Company under the names Veegum Ultra, Veegum HS and Veegum DGT, or calcium silicates, and especially the product in synthetic form sold by the company under the name Micro-cel C.

The term "lipophilic clay" means a clay that is capable of swelling in a lipophilic medium; this clay swells in the medium and thus forms a colloidal dispersion. Examples of lipophilic clays that may be mentioned include modified clays such as modified magnesium silicate (Bentone Gel VS38 from Rheox), and hectorites modified with a $C_{10}$ to C$_{22}$ fatty-acid ammonium chloride, for instance hectorite modified with distearyldimethylammonium chloride (CTFA name: disteardimonium hectorite) sold under the name Bentone 38 CE by the company Rheox or Bentone 38V® by the company Elementis.

In particular, among the gelling agents that may be used, mention may be made of silica particles. Preferably, the silica particles are fumed silica particles.

Suitable silicas include, but are not limited to, hydrophobic silicas, such as pyrogenic silica optionally with hydrophobic surface treatment whose particle size is less than 1 micron, preferably less than 500 nm, preferably less than 100 nm, preferably from 5 nm to 30 nm, including all ranges and subranges therebetween. It is in fact possible to modify the surface of silica chemically, by a chemical reaction producing a decrease in the number of silanol groups present on the surface of the silica. The silanol groups can notably be replaced with hydrophobic groups: a hydrophobic silica is then obtained. The hydrophobic groups can be:

trimethylsiloxyl groups, which are notably obtained by treatment of pyrogenic silica in the presence of hexamethyldisilazane. Silicas treated in this way are called "Silica silylate" according to the CTFA (6th edition, 1995). They are for example marketed under the references "AEROSIL R812®" by the company Degussa, "CAB-O-SIL TS-530®" by the company Cabot;

dimethylsilyloxyl or polydimethylsiloxane groups, which are notably obtained by treatment of pyrogenic silica in the presence of polydimethylsiloxane or dimethyldichlorosilane. Silicas treated in this way are called "Silica dimethyl silylate" according to the CTFA (6th edition, 1995). They are for example marketed under the references "AEROSIL R972®", "AEROSIL R974®" by the company Degussa, "CAB-O-SIL TS-610®", "CAB-O-SIL TS-720®" by the company Cabot.

Preferably, the gelling agent, if present, is present in the composition of the present invention in amounts of active material generally ranging from about 0.1% to about 10%, preferably from about 0.25% to about 5%, and more preferably from about 0.5% to about 3.5%, by weight, based on the total weight of the composition, including all ranges and subranges in between.

According to preferred embodiments of the present invention, methods of treating, caring for and/or making up a keratinous material by applying compositions of the present invention to the keratinous material in an amount sufficient to treat, care for and/or make up the keratinous material are provided. Preferably, "making up" the keratinous material includes applying at least one coloring agent to the keratinous material in an amount sufficient to provide color to the keratinous material.

According to yet other preferred embodiments, methods of enhancing the appearance of a keratinous material by applying compositions of the present invention to the keratinous material in an amount sufficient to enhance the appearance of the keratinous material are provided.

In accordance with the preceding preferred embodiments, the compositions of the present invention are applied topically to the desired area of the keratinous material in an amount sufficient to treat, care for and/or make up the keratinous material, to cover or hide defects associated with keratinous material, or to enhance the appearance of keratinous material. The compositions may be applied to the desired area as needed, preferably once daily, and then preferably allowed to dry before subjecting to contact such as with clothing or other objects. Preferably, the composition is allowed to dry for about 4 minutes or less, more preferably for about 2 minutes or less.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contain certain errors necessarily resulting from the standard deviation found in their respective measurements. The following examples are intended to illustrate the invention without limiting the scope as a result. The percentages are given on a weight basis.

Example 1—Preparation of Foundation Compositions

To prepare foundation compositions, each of phase A and phase B are separately prepared and mixed in a beaker with stirring. Phase A is prepared at 45° C. and Phase B is prepared at 60° C. Phase A is then prepared under high shear and Phase B is slowly added to Phase A to prepare Phase AB. Phase AB is cooled to 35° C. with mixing. Phase C is then added to Phase AB.

| Ingredient Type | Concentration |
|---|---|
| Phase A | |
| Hydrocarbon Fluid | 5-40% |
| Silicone fluid | 10-12% |
| Oil phase Thickeners | 6-9% |
| Emollients | 2-4% |
| Pigments | 5-20% |
| Silicone Dendrimer Acrylate (active) | 0.5%-30% |
| Emulsifiers | 5-8% |
| Phase B | |
| Water phase | 30-35% |
| Preservatives | 1-4% |
| Phase C | |
| Fillers | 1-6% |
| Alcohol | 1-5% |

Example 2—Inventive and Comparative Compositions

Sample "pigment only" formulations were prepared as described in example 1. Different surface-treated pigments were used in different compositions, and the properties resulting from the different "pigment only" compositions were evaluated.

More specifically, foundation compositions containing different surface-treated pigments were tested for adhesion and nontransfer properties. The properties were evaluated through a multichallenge wear test, which is an in vitro test in which a resulting film is abraded one time. In the multichallenge wear test, a numerical rating on a scale of 1-5 was assigned, where 5=least transfer/best film property and 1=most transfer/worst film property.

For the multichallenge wear test, a film is deposited onto a surface such as a black byko-chart Black Scrub Panels P121-10N #5015 using a 1 mL drawdown bar. After drying 24h at 37° C., the deposit can be covered with artificial sebum or sweat. Samples are then abraded using an automatic drawdown machine (Gardco Automatic Drawdown Machine) equipped with Velcro (¾" white 010 PSA 0172) pieces adhered to the lowest bar. Contact between the Velcro adhered bar and the film interface is made and then the bar is automatically dragged across the sample one time. The film can then be wiped by hand using light force with an absorbent material (for example, a large kimwipe). Then, it can be determined how much of the sample remains undisrupted on the scrub panel as well as how much of the sample has transferred to the absorbent material using a rating scale such as the one described above to assess the degree of sample removal from the substrate or the degree of sample transferred to the absorbent material, in which 1 is total disruption and extreme transfer to absorbent material, 2 is most disruption with substantial transfer to absorbent material, 3 is half disruption and some transfer to the absorbent material, 4 is minimal disruption and minimal transfer to absorbent material and 5 is essentially no removal and no transfer.

Results are set forth in Table 1 below.

TABLE 1

| Multiwear Test | | | | | | |
|---|---|---|---|---|---|---|
| | A | B | C | D | E | F |
| Dendritic Silicone Acrylate Copolymer | 0% | 0% | 0% | 0% | 0% | 0% |
| Silicone Elastomer Resin | 0% | 0% | 0% | 0% | 0% | 0% |
| EPF | 12% | 0% | 0% | 0% | 0% | 0% |
| AS | 0% | 12% | 0% | 0% | 0% | 0% |
| FHSA | 0% | 0% | 12% | 0% | 0% | 0% |
| NAI | 0% | 0% | 0% | 12% | 0% | 0% |
| TTB | 0% | 0% | 0% | 0% | 12% | 0% |
| ITT | 0% | 0% | 0% | 0% | 0% | 12% |
| TTB | 0% | 0% | 0% | 0% | 0% | 0% |
| ASC | 0% | 0% | 0% | 0% | 0% | 0% |
| FHTS | 0% | 0% | 0% | 0% | 0% | 0% |
| FHS | 0% | 0% | 0% | 0% | 0% | 0% |
| Volatile Oils | 15-50% | 15-50% | 15-50% | 15-50% | 15-50% | 15-50% |
| Oil phase Thickeners | 6-9% | 6-9% | 6-9% | 6-9% | 6-9% | 6-9% |
| Emollients | 2-4% | 2-4% | 2-4% | 2-4% | 2-4% | 2-4% |
| Pigments | 5-20% | 5-20% | 5-20% | 5-20% | 5-20% | 5-20% |
| Water phase | 35-50% | 35-50% | 35-50% | 35-50% | 35-50% | 35-50% |

| | EPF | AS | FHSA | NAI | TTB | ITT |
|---|---|---|---|---|---|---|
| Abrasion with Sebum | 2 | 1 | 3 | 1 | 1 | 2 |
| Abrasion with Sweat | 2 | 1 | 2 | 1 | 1 | 2 |
| Abrasion Dry | 2 | 2 | 2 | 2 | 1 | 2 |
| Transfer | 2 | 3 | 2 | 2 | 3 | 2 |
| Average per Category | 2 | 1.75 | 2.25 | 1.5 | 1.5 | 2 |

TABLE 1-continued

| Multiwear Test | | | | |
|---|---|---|---|---|
| | G | H | I | J |
| Dendritic Silicone Acrylate Copolymer | 0% | 0% | 0% | 0% |
| Silicone Elastomer Resin | 0% | 0% | 0% | 0% |
| EPF | 0% | 0% | 0% | 0% |
| AS | 0% | 0% | 0% | 0% |
| FHSA | 0% | 0% | 0% | 0% |
| NAI | 0% | 0% | 0% | 0% |
| TTB | 0% | 0% | 0% | 0% |
| ITT | 0% | 0% | 0% | 0% |
| TTB | 12% | 0% | 0% | 0% |
| ASC | 0% | 12% | 0% | 0% |
| FHTS | 0% | 0% | 12% | 0% |
| FHS | 0% | 0% | 0% | 12% |
| Volatile Oils | 15-50% | 15-50% | 15-50% | 15-50% |
| Oil phase Thickeners | 6-9% | 6-9% | 6-9% | 6-9% |
| Emollients | 2-4% | 2-4% | 2-4% | 2-4% |
| Pigments | 5-20% | 5-20% | 5-20% | 5-20% |
| Water phase | 35-50% | 35-50% | 35-50% | 35-50% |

| | TTB | ASC | FHTS | FHS |
|---|---|---|---|---|
| Abrasion with Sebum | 2 | 1 | 2 | 2 |
| Abrasion with Sweat | 1 | 2 | 2 | 2 |
| Abrasion Dry | 1 | 2 | 2 | 2 |
| Transfer | 3 | 1 | 1 | 2 |
| Average per Category | 1.75 | 1.5 | 1.75 | 2 |

EPF - Sodium perfluorohexylethylphosphonate
AS (OTS) - "Alkyl Silane" - Triethoxy caprylylsilane
FHSA - FHS and ASC hybrid
NAI - Disodium Stearoyl Gutamate
TTB - Iron oxide (and) isopropyl titanium triisosterate (and) triethoxysilylethyl polydimethylsiloxy ethyl dimethicone
ITT - "organo titanate" isopropyl titanium triisosterate
ASC - Acrylates/Dimethicone Copolymer
FHTS - FHS and AS hybrid
FHS - Perfluorooctyltriethoxysilane An extreme multichallenge wear test was also used to evaluate compositions containing silicone acrylate copolymer/silicone elastomer resin as well as different surface-treated pigments using the same protocol as above, except dragging the bar across the sample 10 times.

Results are set forth in Table 2 below.

TABLE 2

Extreme Multiwear Test

|  | Inventive A | Comparative B | Inventive C | Comparative D | Inventive E | Comparative F |
|---|---|---|---|---|---|---|
| Dendritic Silicone Acrylate Copolymer | 10% | 10% | 10% | 10% | 10% | 10% |
| Silicone Elastomer Resin | 1% | 1% | 1% | 1% | 1% | 1% |
| EPF | 12% | 0% | 0% | 0% | 0% | 0% |
| AS | 0% | 12% | 0% | 0% | 0% | 0% |
| FHSA | 0% | 0% | 12% | 0% | 0% | 0% |
| NAI | 0% | 0% | 0% | 12% | 0% | 0% |
| TTB | 0% | 0% | 0% | 0% | 12% | 0% |
| ITT | 0% | 0% | 0% | 0% | 0% | 12% |
| TTB | 0% | 0% | 0% | 0% | 0% | 0% |
| ASC | 0% | 0% | 0% | 0% | 0% | 0% |
| FHTS | 0% | 0% | 0% | 0% | 0% | 0% |
| FHS | 0% | 0% | 0% | 0% | 0% | 0% |
| Volatile Oils | 15-50% | 15-50% | 15-50% | 15-50% | 15-50% | 15-50% |
| Oil phase Thickeners | 6-9% | 6-9% | 6-9% | 6-9% | 6-9% | 6-9% |
| Emollients | 2-4% | 2-4% | 2-4% | 2-4% | 2-4% | 2-4% |
| Pigments | 5-20% | 5-20% | 5-20% | 5-20% | 5-20% | 5-20% |
| Water phase | 35-50% | 35-50% | 35-50% | 35-50% | 35-50% | 35-50% |

|  | EPF | AS | FHSA | NAI | TTB | ITT |
|---|---|---|---|---|---|---|
| Abrasion with Sebum | 4 | 2 | 3.5 ± 0.71 | 3 | 3 | 2.5 ± 0.71 |
| Abrasion with Sweat | 4.25 ± 0.35 | 2 | 4 | 1.75 ± 0.35 | 2.25 ± 0.35 | 3 |
| Abrasion Dry | 5 | 5 | 5 | 4 | 5 | 5 |
| Transfer Sebum | 4 | 1.5 ± 0.71 | 4 | 2 | 3 | 2 |
| Transfer Sweat | 5 | 4 | 5 | 4 | 4.5 ± 0.71 | 4 |
| Average per Category | 4.45 | 2.9 | 3.625 | 2.95 | 3.55 | 3.3 |

|  | Comparative G | Comparative H | Inventive I | Inventive J |
|---|---|---|---|---|
| Dendritic Silicone Acrylate Copolymer | 10% | 10% | 10% | 10% |
| Silicone Elastomer Resin | 1% | 1% | 1% | 1% |
| EPF | 0% | 0% | 0% | 0% |
| AS | 0% | 0% | 0% | 0% |
| FHSA | 0% | 0% | 0% | 0% |
| NAI | 0% | 0% | 0% | 0% |
| TTB | 0% | 0% | 0% | 0% |
| ITT | 0% | 0% | 0% | 0% |
| TTB | 12% | 0% | 0% | 0% |
| ASC | 0% | 12% | 0% | 0% |
| FHTS | 0% | 0% | 12% | 0% |
| FHS | 0% | 0% | 0% | 12% |
| Volatile Oils | 15-50% | 15-50% | 15-50% | 15-50% |
| Oil phase Thickeners | 6-9% | 6-9% | 6-9% | 6-9% |
| Emollients | 2-4% | 2-4% | 2-4% | 2-4% |
| Pigments | 5-20% | 5-20% | 5-20% | 5-20% |
| Water phase | 35-50% | 35-50% | 35-50% | 35-50% |

TABLE 2-continued

| | Extreme Multiwear Test | | | |
|---|---|---|---|---|
| | TTB | ASC | FHTS | FHS |
| Abrasion with Sebum | 2.5 ± 0.71 | 2.5 ± 0.71 | 3.5 ± 0.71 | 4.25 ± 0.35 |
| Abrasion with Sweat | 3 | 3 | 4 | 4.5 ± 0.71 |
| Abrasion Dry | 5 | 5 | 5 | 5 |
| Transfer Sebum | 2.5 ± 0.71 | 2 ± 0.141 | 2.5 ± 0.71 | 4 |
| Transfer Sweat | 4 | 4 | 4.5 ± 0.71 | 5 |
| Average per Category | 3.4 | 3.3 | 3.9 | 4.55 |

W/S foundations were explored for their excellent non-transfer, artificial sebum resistance, and artificial sweat resistance. The combination of dendritic silicone acrylate copolymer/silicone elastomer resin was explored in combination with various surface-treated pigments in W/S foundation formulas.

Formulas with only surface-treated pigments without the combination of the silicone acrylate copolymer/silicone elastomer resin were assessed by the multichallenge wear test (Table 1—"pigment only"). Overall the pigments alone did not provide substantive level of transfer resistance or sebum/sweat resistance, regardless of the surface-treated pigment used. The "AS, NAI, ASC, TTB pigment only" performed poorly for sebum and sweat resistance, "FHS, FHTS, EPF and ITT pigment only" samples performed fairly, and the "FHSA pigment only" sample comparatively performed the best of all pigment only samples tested for sebum resistance.

Compositions containing silicone acrylate copolymer/silicone elastomer resin (Table 2) were tested with a more extreme multichallenge test to discriminate performance. Of the samples made that combined dendritic silicone acrylate and silicone elastomer resin with surface-treated pigments, the samples that performed extremely well in terms of sebum resistance, sweat resistance and transfer resistance were the FHS and secondarily the EPF, FHSA, FHTS and TTB treated pigments. This was surprising as the "pigment only" samples performed differently.

What is claimed is:

1. A composition comprising at least one dendritic silicone acrylate copolymer, at least one silicone elastomer resin, and at least one surface-treated pigment having a surface treatment comprising at least one selected from the group consisting of organosilanes and halogenated organosilanes, wherein the composition is in the form of an emulsion and wherein the surface-treated pigment is present in the composition in an amount ranging from 5% to 20%, by weight with respect to the total weight of the composition.

2. The composition of claim 1, wherein the composition is in the form of a water-in-oil emulsion.

3. The composition of claim 1, wherein the composition is in the form of an oil-in-water emulsion.

4. The composition of claim 1, wherein the surface treatment is selected from the group consisting of perfluorooctyltriethoxysilane, perfluorooctyltriethoxysilane/acrylates dimethicone copolymer, perfluorooctyltriethoxysilane/triethoxy caprylylsilane, and mixtures thereof.

5. The composition of claim 4, wherein the silicone elastomer resin is selected from the group consisting of vinyldimethyl/trimethylsiloxysilicate stearyl dimethicone crosspolymer, dimethicone/vinyltrimethylsiloxysilicate crosspolymer, and mixtures thereof.

6. The composition of claim 5, wherein the dendritic silicone acrylate copolymer is acrylates/polytrimethylsiloxymethacrylate copolymer.

7. The composition of claim 6, wherein the dendritic silicone acrylate copolymer and silicone elastomer resin are present in the compositions in an active solid content weight ratio of 1:50 to 70:1.

8. The composition of claim 7, wherein the surface-treated pigment and silicone elastomer resin are present in the compositions in an active solid content weight ratio of 1:4 to 50:1.

9. The composition of claim 8, wherein the dendritic silicone acrylate copolymer and surface-treated pigment are present in the compositions in an active solid content weight ratio of 1:34 to 25:3.

10. The composition of claim 1, wherein the composition further comprises at least one coloring agent which is a non-surface treated pigment.

11. The composition of claim 1, wherein the silicone elastomer resin comprises at least one trimethylsiloxysilicate group.

12. The composition of claim 11, wherein the silicone elastomer resin is selected from the group consisting of vinyldimethyl/trimethylsiloxysilicate stearyl dimethicone crosspolymer, dimethicone/vinyltrimethylsiloxysilicate crosspolymer, and mixtures thereof.

13. The composition of claim 1, wherein the dendritic silicone acrylate copolymer is acrylates/polytrimethylsiloxymethacrylate copolymer.

14. The composition of claim 1, further comprising at least one volatile oil.

15. The composition of claim 14, wherein the volatile oil is selected from the group consisting of cyclopentasiloxane, isododecane, and mixtures thereof.

16. The composition of claim 1, wherein the dendritic silicone acrylate copolymer and silicone elastomer resin are present in the compositions in an active solid content weight ratio of 1:300 to 400:1.

17. The composition of claim 16, wherein the surface-treated pigment and silicone elastomer resin are present in the compositions in an active solid content weight ratio of 1:15 to 300:1.

18. The composition of claim 17, wherein the dendritic silicone acrylate copolymer and surface-treated pigment are present in the compositions of the present invention in an active solid content weight ratio of 1:300 to 30:1.

19. An emulsion composition comprising:
- at least one acrylates/polytrimethylsiloxymethacrylate copolymer,
- at least one silicone elastomer resin, wherein the silicone elastomer resin is selected from the group consisting of vinyldimethyl/trimethylsiloxysilicate stearyl dimethicone crosspolymer, dimethicone/vinyltrimethylsiloxysilicate crosspolymer, and mixtures thereof, and
- at least one surface-treated pigment having a surface treatment comprising halogenated organosilane,
- wherein the dendritic silicone acrylate copolymer and silicone elastomer resin are present in the compositions in an active solid content weight ratio of 1:50 to 70:1,
- wherein the surface-treated pigment and silicone elastomer resin are present in the compositions in an active solid content weight ratio of 1:4 to 50:1,
- wherein the surface-treated pigment is present in the composition in an amount ranging from 5% to 20%, by weight with respect to the total weight of the composition; and
- wherein the dendritic silicone acrylate copolymer and surface-treated pigment are present in the compositions of the present invention in an active solid content weight ratio of 1:34 to 25:3.

20. The composition of claim 19, wherein the surface-treated pigment is selected from the group consisting of perfluorooctyltriethoxysilane, perfluorooctyltriethoxysilane/acrylates dimethicone copolymer, perfluorooctyltriethoxysilane/triethoxy caprylylsilane, and mixtures thereof.

21. A method of making up a keratinous substrate comprising applying the composition of claim 1 to a keratinous substrate in an amount sufficient to makeup the keratinous substrate.

* * * * *